US008309749B2

(12) United States Patent
Fang et al.

(10) Patent No.: US 8,309,749 B2
(45) Date of Patent: Nov. 13, 2012

(54) PROCESS OF MAKING ALUMINOXANE AND CATALYSTS CONTAINING THUS PREPARED ALUMINOXANE

(75) Inventors: Xinggao Fang, Richmond, VA (US); Timothy A. Boyer, Eldersburg, MD (US); John Henry Hain, Jr., Woodstock, MD (US)

(73) Assignee: W R Grace & Co-Conn, Columbia, MD (US)

( * ) Notice: Subject to any disclaimer, the term of this patent is extended or adjusted under 35 U.S.C. 154(b) by 0 days.

(21) Appl. No.: 13/320,144

(22) PCT Filed: Jun. 9, 2010

(86) PCT No.: PCT/US2010/001651
§ 371 (c)(1),
(2), (4) Date: Nov. 11, 2011

(87) PCT Pub. No.: WO2010/144130
PCT Pub. Date: Dec. 16, 2010

(65) Prior Publication Data
US 2012/0071679 A1  Mar. 22, 2012

Related U.S. Application Data

(60) Provisional application No. 61/186,090, filed on Jun. 11, 2009.

(51) Int. Cl.
*C07F 5/06* (2006.01)
*B01J 31/00* (2006.01)
(52) U.S. Cl. .......... 556/181; 556/173; 556/11; 502/104; 502/118
(58) Field of Classification Search .................. 556/11, 556/173, 181; 502/104, 118
See application file for complete search history.

(56) References Cited

U.S. PATENT DOCUMENTS

| 4,404,344 A | 9/1983 | Sinn et al. ............... 526/160 |
| 4,730,071 A | 3/1988 | Schoenthal et al. ....... 556/179 |
| 4,730,072 A | 3/1988 | Schoenthal et al. ....... 556/179 |
| 4,908,463 A | 3/1990 | Bottelberghe ............ 556/179 |
| 4,912,075 A | 3/1990 | Chang .................... 502/107 |
| 4,924,018 A | 5/1990 | Bottelberghe ............ 556/179 |
| 4,935,397 A | 6/1990 | Chang .................... 502/117 |
| 4,937,217 A | 6/1990 | Chang .................... 502/111 |
| 4,968,827 A | 11/1990 | Davis .................... 556/179 |
| 5,041,585 A | 8/1991 | Deavenport et al. ...... 556/179 |
| 5,064,802 A | 11/1991 | Stevens et al. .......... 502/155 |
| 5,084,585 A | 1/1992 | Maezawa et al. ......... 556/179 |
| 5,087,713 A | 2/1992 | Sinn et al. .............. 556/179 |
| 5,099,050 A | 3/1992 | Sangokoya .............. 556/179 |
| 5,157,008 A | 10/1992 | Sangokoya et al. ....... 502/111 |
| 5,206,401 A | 4/1993 | Deavenport et al. ...... 556/175 |
| 5,225,500 A | 7/1993 | Elder et al. ............. 526/127 |
| 5,243,002 A | 9/1993 | Razavi .................. 526/170 |
| 5,321,106 A | 6/1994 | LaPointe ................ 526/126 |
| 5,427,991 A | 6/1995 | Turner ................... 502/103 |
| 5,427,992 A | 6/1995 | Graefe et al. ........... 502/111 |
| 5,578,537 A | 11/1996 | Herrmann et al. ........ 502/120 |
| 5,643,847 A | 7/1997 | Walzer, Jr. .............. 502/117 |
| 5,663,394 A | 9/1997 | Roberg et al. ........... 556/179 |
| 5,693,838 A | 12/1997 | Sangokoya et al. ....... 556/179 |
| 5,728,640 A | 3/1998 | Lu et al. ................ 502/107 |
| 5,756,607 A | 5/1998 | Lux et al. ............... 526/127 |
| 5,789,332 A | 8/1998 | Kutschera et al. ........ 502/106 |
| 5,866,663 A | 2/1999 | Brookhart et al. ........ 526/170 |
| 5,880,056 A | 3/1999 | Tsutsui et al. ........... 502/103 |
| 5,880,323 A | 3/1999 | Brookhart, III et al. ... 585/527 |
| 5,886,224 A | 3/1999 | Brookhart et al. ........ 564/272 |
| 5,891,963 A | 4/1999 | Brookhart et al. ....... 525/326.1 |
| 5,902,891 A | 5/1999 | Sangokoya et al. ....... 556/179 |
| 6,124,229 A | 9/2000 | Becker et al. ........... 502/102 |
| 6,159,888 A | 12/2000 | Welch et al. ............ 502/117 |
| 6,559,090 B1 | 5/2003 | Shih ..................... 502/152 |
| 6,943,224 B2 | 9/2005 | Shih ..................... 526/113 |

FOREIGN PATENT DOCUMENTS

| EP | 426637 | 5/1991 |
| EP | 426638 | 5/1991 |
| WO | 98/27124 | 6/1998 |
| WO | 98/30612 | 7/1998 |
| WO | 99/46302 | 9/1999 |
| WO | 99/46303 | 9/1999 |
| WO | 99/46304 | 9/1999 |

OTHER PUBLICATIONS

Kanicky, J.R. et al., "Surface Chemistry in the Petroleum Industry", Handbook of Applied Surface and Colloid Chemistry, K. Homberg (ed.), Chapter 11, p. 251-267.
Griffin, W. C., "Classification of Surface-Active Agents by HLB", Journal of the Society of Cosmetic Chemists, 1949, pp. 311-326.

*Primary Examiner* — Porfirio Nazario Gonzalez
(74) *Attorney, Agent, or Firm* — Robert A. Maggio; Harvey L. Cohen

(57) ABSTRACT

Processes for preparing aluminoxane comprising: bringing into contact under reaction conditions in an inert atmosphere a liquid containing reaction mixture comprising: (i) a water in oil emulsion comprising water and at least one emulsifier in a first hydrocarbon solvent; and (ii) an organoaluminum compound capable of forming aluminoxane in a second hydrocarbon solvent; provided that the aluminoxane produced by the reaction is present in solution under the reaction conditions. In a preferred embodiment a support carrier for the aluminoxane: (i) is present during the contact step or (ii) is introduced following contact. A polymerization catalyst can be prepared wherein the support carrier is SiO2 and a Group 3 to Group 10 metal containing single site complex is mixed with the aluminoxane. Catalysts suitable for polymerizing an olefin such as ethylene or copolymerizing an olefin with at least one $C_3$ to $C_{20}$ alpha-olefin can be produced.

18 Claims, No Drawings

PROCESS OF MAKING ALUMINOXANE AND CATALYSTS CONTAINING THUS PREPARED ALUMINOXANE

CROSS-REFERENCE TO RELATED APPLICATIONS

This application claims the benefit of the filing date of U.S. Provisional Patent Application No. 61/186,090 filed Jun. 11, 2009, the disclosure of which is hereby incorporated herein by reference.

BACKGROUND OF THE INVENTION

Embodiments of the present invention relate to processes for preparing aluminoxane (sometimes referred to as alumoxane) or aluminoxane derivatives, supported aluminoxane or aluminoxane derivatives, supported single site/aluminoxane catalysts, and the products, including polymer polymerization products produced in accordance with the processes described.

Catalyst compositions comprising organometallic complex compounds generally including single site catalysts, such as metallocenes, in combination with aluminoxane are known for the polymerization of olefins and such catalysts are generally considered valuable due to their good activity, in other words, the ability to produce a high quantity of olefin polymer for each gram of catalyst. Additionally, properties of polymers produced using such catalysts can be affected not only by polymerization process conditions but also by characteristics of the catalyst composition such as its chemical composition, morphology and the like. Thus, improvements in methods for producing aluminoxane for use in such catalyst compositions are desirable.

BRIEF SUMMARY OF THE INVENTION

An embodiment of the invention comprises a process for preparing aluminoxane comprising: (a) bringing into contact under reaction conditions in an inert atmosphere a reaction mixture comprising: (i) a water in oil emulsion comprising water and at least one emulsifier in a first hydrocarbon solvent; and (ii) an organoaluminum compound capable of forming alumoxane in a second hydrocarbon solvent; wherein: (b) the molar ratio of the organoaluminum compound to water present in the emulsion is about 0.6 to about 2:1; and (c) the aluminoxane produced by the reaction is present in solution; provided that the first and second hydrocarbon solvents in step (a) maintain the aluminoxane in solution under the reaction conditions.

Another embodiment comprises a process for preparing aluminoxane comprising: (a) combining a first hydrocarbon solvent, water, and at least one emulsifier to form an emulsion: (i) wherein the volume ratio of said first hydrocarbon solvent, water, and emulsifier is about 100 (solvent):about 5 to about 100 (water):about 0.05 to about 20 (emulsifier); (b) dissolving an organoaluminum compound capable of forming aluminoxane in a second hydrocarbon solvent to form a solution comprising about 5 to about 40% by weight of the organoaluminum compound; (c) contacting the emulsion and the solution with one another: (i) in a molar ratio of the organoaluminum compound to water in the emulsion of about 0.6 to about 2:1; and (ii) in an inert atmosphere; to produce an aluminoxane solution, provided that the first and second hydrocarbon solvents present in steps (a) and (b) maintain the aluminoxane in solution under the reaction conditions in step (c).

In a preferred embodiment of the process a support carrier for the aluminoxane: (i) is present during the contact steps described above; or (ii) is introduced following the contact steps.

In still another embodiment a polymerization catalyst is prepared using the above processes and wherein the support carrier is $SiO_2$ and a Group 3 to Group 10 metal-containing single site complex is mixed with the aluminoxane to produce a catalyst suitable for homopolymerizing an olefin such as ethylene or copolymerizing an olefin with at least one $C_3$ to $C_{20}$ alpha-olefin monomer to form a polymer under olefin polymerization conditions. In a particularly preferred embodiment, the single site complex is a metallocene and the aluminoxane is methylaluminoxane (MAO).

DETAILED DESCRIPTION

As used herein the following terms or phrases have the indicated meanings.

Aluminoxane (or alumoxane) is generally understood by those skilled in the art to refer to a class of compounds, including mixtures of compounds, having a linear or cyclic structure, or a mixture of linear and cyclic structures, as shown by the chemical formulas below:

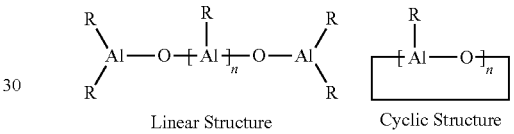

Linear Structure          Cyclic Structure wherein in the above formulas, R is a hydrocarbon group, such as an alkyl group of 1 to 20 carbon atoms, preferably 1 to 12 carbon atoms, more preferably 1 to 6 carbon atoms, such as methyl, ethyl, propyl, isopropyl, sec-butyl, isobutyl, tert-butyl, pentyl, hexyl, and is more preferably $C_1$-$C_5$ alkyl, particularly methyl; an alkenyl group of 2 to 20 carbon atoms, preferably 2 to 12 carbon atoms; an aryl group of 6 to 20 carbon atoms, preferably 6 to 12 carbon atoms; or an arylalkyl group of 7 to 20 carbon atoms, preferably 7 to 12 carbon atoms; and n is an integer indicating a degree of polymerization and is typically about 2 to about 50, preferably about 5 to about 40, more preferably about 7 to about 35.

Furthermore, for purposes of the present invention, aluminoxane includes not only the compounds and structures immediately above, but also derivatives, complexes and/or associations of such compounds with at least one emulsifier or surfactant compound used in the process of producing such aluminoxane.

The term "hydrocarbyl substituent" or "hydrocarbyl group" is used in its ordinary sense, which is well known to those skilled in the art. Specifically, it refers to a group having a carbon atom directly attached to the remainder of the molecule and having predominantly hydrocarbon character. Examples of hydrocarbyl groups include: (1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical); (2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy); (3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every about ten carbon atoms in the hydrocarbyl group.

The term "lower" when used in conjunction with terms such as alkyl, alkenyl, and alkoxy, is intended to describe such groups that contain a total of up to about 8 carbon atoms.

The term "emulsion" refers to a mixture or dispersion of at least two immiscible substances, liquids in the present invention, in which one substance, the dispersed phase, is dispersed in the other substance, the continuous phase. An emulsion is stabilized, in other words the dispersed phase remains dispersed during the relevant time period, such as during storage and/or immediately prior to and during use, with the assistance of one or more substances known as emulsifiers. An emulsion can be a water-in-oil emulsion or an oil-in-water emulsion depending on such variables as the amount of oil (as well as type of oil) and water present, the conditions used to prepare the emulsion, the emulsifier type and amount, the temperature and combinations of such variables. The particle size or droplet size of the dispersed phase can vary over a significant range and the emulsion can remain stable, but its properties and suitability for a specific use may vary depending on the particle size of the dispersed phase. Particle size is typically expressed in terms of mean or average size since the uniformity of the dispersed phase can also vary depending on the variables noted above. Particle size does not require that the particles are necessarily spheres and the size of the particles can be based on a major or average dimension of each particle, although in a system comprising a dispersed liquid phase in a continuous liquid phase, fluid dynamics suggest that the dispersed particles will tend to be substantially spherical.

The term "emulsifier" refers to a compound or mixture of compounds that has the capacity to promote formation of an emulsion and/or substantially stabilize an emulsion, at least for the short-term, i.e., during the time of practical or commercial interest, such as during storage or during use or both. An emulsifier provides stability against significant or substantial aggregation or coalescence of the dispersed phase of an emulsion. An emulsifier is typically considered to be a surface active substance in that it is capable of interacting with the dispersed and continuous phases of an emulsion at the interface between the two. For purposes herein a "surfactant" and an "emulsifier" are considered equivalent or interchangeable terms. Furthermore, included within the scope of the generic term "surfactant" are the various types of surfactants such as nonionic, ionic or partially ionic, anionic, amphoteric, cationic and zwitterionic surfactants.

The term "solvent" as used in the present disclosure means one or more hydrocarbon solvents and it is used in its generic sense of a diluent except where the context of the disclosure requires a particular component (the solute) to be dissolved, in which case the solvent is suitable for substantially dissolving the component under the given conditions to form a uniformly dispersed mixture (solution) at the molecular or ionic size level. Thus, reference to a solvent does not preclude the possibility that the solute or dissolved component is in equilibrium with an undissolved portion of the solute, provided that the amount that is not dissolved does not exceed about 10 wt. % of the total solute present (dissolved plus undissolved); alternatively about 5 wt. %; for example, about 2 wt. %. Otherwise, a "solvent" can be understood to refer to a diluent, for example, where such diluent is a liquid that is suitable for forming an emulsion in which water is dispersed in the diluent using at least one emulsifier or surfactant. In the present disclosure a suitable liquid can be both a diluent and a solvent for different components that are present, for example, toluene can be a diluent in which water is dispersed to form an emulsion and it can also be a solvent (or a component of a mixed solvent) for aluminoxane that is formed from the reaction of water with an organoaluminum compound. Hydrocarbon solvents comprise carbon and hydrogen, but other atoms can also be present, such as chlorine or bromine.

For purposes of the present invention, "solvent" or "diluent" is also understood to include the term "oil" when oil is used in the context of the diluent that is used to prepare a water-in-oil emulsion. Oils useful in the present invention include compositions that are typically referred to as oils, such as mineral oil, highly refined mineral oil, ultra refined mineral oil and polyalphaolefin (PAO) and also hydrocarbon solvents or diluents, other than polar solvents and diluents.

The terms "stability" or "stable" when used in reference to an emulsion refer to the dispersed, aqueous or hydrophilic phase (for example, water) remaining dispersed or substantially dispersed in the lipophilic phase (organic solvent, as herein). In other words, substantially no phase separation occurs as indicated by visual observation after a period of about 72 hours; alternatively, no visual separation occurs in the emulsion for the period of time between its preparation and use in a reaction mixture to prepare aluminoxane.

Generally, aluminoxane is prepared according to various embodiments of the present invention by reacting an organoaluminum compound to form aluminoxane, including, for example, a $C_1$ to $C_5$ trialkyl aluminum compound, dispersed or dissolved in a suitable solvent, with an emulsion comprising water, an emulsifier and a suitable diluent or solvent. The aluminoxane preferably remains in solution following its formation. Examples of organoaluminum compounds useful for preparing the aluminoxane include: trialkylaluminum compounds, such as trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, trihexylaluminum, trioctylaluminum and tridecylaluminum; tricycloalkylaluminum compounds, such as tricyclohexylaluminum and tricyclooctylaluminum; dialkylaluminum halide compounds, such as dimethylaluminum chloride, diethylaluminum chloride, diethylaluminum bromide and diisobutylaluminum chloride; dialkylaluminum hydride compounds, such as diethylaluminum hydride and diisobutylaluminum hydride; dialkylaluminum alkoxide compounds, such as dimethylaluminum methoxide and diethylaluminum ethoxide; and dialkylaluminum aryloxide compounds, such as diethylaluminum phenoxide. Preferred are trialkylaluminum and tricycloalkylaluminum compounds; particularly preferred is trimethylaluminum.

Oils suitable for use in the present invention include solvents or diluents that can be used to prepare a water-in-oil emulsion. Such oils include compositions that are typically referred to as oils, such as mineral oil, highly refined mineral oil, ultra refined mineral oil and low molecular weight polyalphaolefins (PAO), as well as petroleum fractions, such as gasoline, kerosene and gas oil. Oils also include hydrocarbon solvents or diluents, other than polar solvents and diluents. Particularly useful oils include aromatic hydrocarbons or aromatic solvents, such as benzene, toluene, xylene, p-xylene, m-xylene, o-xylene, mixtures of the xylenes, cumene, cymene, ethylbenzene, propylbenzene, and the like, as well as halides of these aromatic hydrocarbons, particularly chlorides and bromides thereof; and mixtures of the above. Toluene is particularly preferred as it is useful for preparing a water-in-oil emulsion for the purpose of introducing water as a reactant, and aluminoxane produced by the reaction is substantially soluble in toluene under the reaction conditions. One skilled in the art will also take into consideration factors such as cost and safety, including the potential for ignition of a solvent, diluent or oil under reaction conditions, including conditions used to prepare the water-in-oil emulsion, particularly if high energy input is used, such as high shear, high speed impellers or other devices.

Saturated aliphatic compounds such as butane, pentane, hexane, heptane, octane, isoctane, and the like are not preferred since the aluminoxane that is formed is typically not soluble in such solvents. However, provided that the solvents used to dissolve the organoaluminum compound and to form the water emulsion, which solvents may be the same or different or may themselves be mixtures, are capable of maintaining the aluminoxane reaction product in solution under the reaction conditions used for its synthesis, the individual character of each of the solvents or mixtures is not critical. Alternatively, cycloaliphatic compounds such as cyclobutane, cyclopentane, cyclohexane, cycloheptane, methylcyclopentane, dimethylcyclopentane, and the like; alkenes and cycloalkenes such as butene, hexene, cyclohexene, octene, and the like may also be useful, subject to the above proviso and further that there is present a sufficient amount of a solvent in which aluminoxane formed during the reaction can remained dissolved under the reaction conditions. Significant attributes of the solvent, diluent or mixtures of solvents/diluents are that it be liquid at the reaction temperature, that it does not react with the organoaluminum compound or with water or interfere to a significant extent in any subsequent reaction wherein the aluminoxane is supported and/or used to prepare polymerization catalysts. In particular, diluents or solvents or mixtures thereof must be oxygen-free. Similarly, hydroxyl groups, ether groups, carboxyl groups, keto groups and the like can adversely affect aluminoxane synthesis and are to be avoided.

To carry out the reaction, the organoaluminum compound is dissolved in a hydrocarbon solvent, also referred to herein as a "second" hydrocarbon solvent, and it is brought into reactive contact with the water-in-oil emulsion, wherein the oil is also referred to as the "first" hydrocarbon solvent or oil. It is preferred that the organoaluminum compound be soluble or substantially soluble in the second solvent at the reaction temperature. For purposes of the present invention, the first and second solvents can be the same, for example, toluene. Furthermore, the aluminoxane produced by the reaction should also be soluble in the solvent or solvents used. Generally, the organoaluminum compound, a hydrocarbyl aluminum compound such as trialkyl aluminum, is present in solution in an anhydrous, inert organic solvent. Typically, the concentration of the organoaluminum compound is about 2 percent by weight aluminum compound to a concentration at which it remains soluble in the solvent at reaction conditions. Useful concentrations include about 5 percent to about 40 percent by weight based on the total weight of the solution; alternatively about 5 to about 30 percent; for example about 10 to about 20 percent by weight. Suitable solvents include a normally liquid hydrocarbon solvent such as an aromatic hydrocarbon (unsubstituted or alkyl-substituted or cycloalkyl-substituted), such as benzene, toluene, xylene (including ortho-, meta- and para-xylene and mixtures thereof), ethylbenzene, propylbenzene, cumene and mixtures thereof. Toluene is particularly preferred.

The amount of water that can be dispersed or form an emulsion in the oil or organic solvent or diluent ranges from just above the limits of solubility of water in the solvent to about 50% by weight, based on the weight of the water and diluent or more, depending on the emulsifier, surfactant or mixture of surfactants used and the conditions of forming an emulsion. The amount of water can be selected as necessary in order to efficiently carry out the reaction with the organoaluminum compound at the reaction temperature and for the reaction time desired. Furthermore, it is desirable to avoid the presence of excess water in the reaction mixture in order to avoid undesirable reactions with the organoaluminum compound or with the resulting aluminoxane.

Suitable organoaluminum compounds are selected from the group consisting of alkyl aluminium, aryl aluminium and alkyl aluminium halide; preferably trialkyl aluminium; more preferably tri($C_1$ to about $C_6$ alkyl) aluminium; a particularly preferred organoaluminum compound is trimethyl aluminium.

In general, the mole ratio of the organoaluminum compound to water in the reaction mixture will be about 1:1 although variations of this ratio can be used without adversely affecting the aluminoxane product. For example, the ratio can vary from about 0.5:1 to about 2:1; preferably about 0.6:1 to about 1.75:1; alternatively about 0.7:1 to about 1.5:1; for example, about 0.8:1 to about 1.4:1; such as about 0.9:1 to about 1.25:1; for example, about 1 to 1.5:1.

After reaction, the solvent can be stripped and the aluminoxane isolated as a stable powder. Alternatively, the aluminoxane can be left dissolved in the solvent, and the aluminoxane composition can be separated from unreacted organoaluminum compound, such as by the addition of a non-solvent for one of the components, e.g., the aluminoxane, followed by filtration, and the aluminoxane reacted with one or more suitable transition metal compounds to form polymerization catalysts. In another alternative embodiment, the aluminoxane reaction is carried out in the presence of a suitable carrier for the aluminoxane or a suitable carrier is added to the reaction mixture during reaction or synthesis of the aluminoxane. Solvent (and other by-products, if any) can be removed using an appropriate extraction or drying process step in order to produce aluminoxane supported on the carrier. If desired, the aluminoxane (in solution in the reaction mixture or in substantially dried form) can be mixed with an inert solvent in which the aluminoxane is substantially insoluble in order to extract or wash non-aluminoxane components and further purify the aluminoxane. Such solvents include, for example, saturated hydrocarbons such as pentane, hexane, heptane, octane, decane, and the like; a preferred inert solvent is pentane. The above alternative process steps are preferably carried out under an inert atmosphere.

Processes of the invention, including synthesis of the aluminoxane and preparation of catalysts comprising aluminoxane are typically conducted under an inert atmosphere; useful inert gasses include nitrogen, helium, argon, methane and mixtures thereof.

Aluminoxane produced by the processes herein are particularly useful for preparing polymerization catalysts generally referred to as single site catalysts comprising organometallic complex compounds. Such single site catalysts are well known in the art and include metallocenes, constrained geometry compounds, bidentate and tridentate transition metal catalysts and the like. Suitable polymerization catalysts are described, for example, in U.S. Pat. No. 6,559,090 (K-Y. Shih et al.) and U.S. Pat. No. 6,943,224 (K-Y. Shih), and the further patent references cited therein, incorporated herein by reference to the extent permitted. For example, as described in U.S. Pat. No. 6,943,224, single-site catalyst systems are characterized by the fact that their metal centers behave alike during polymerization thus making very uniform polymers. Catalysts are judged to behave in a single-site manner when the polymer they make meets some basic criteria (e.g., narrow molecular weight distribution, or uniform comonomer distribution). Thus, the metal can have any ligand set around it and be classified as "single-site" as long as the polymer that it produces has certain properties. Included within single-site catalyst systems are metallocene catalysts and constrained geometry catalysts. A "metallocene" is conventionally understood to mean a metal (e.g., Zr, Ti, Hf, V or La) complex that is bound to two cyclopentadienyl (Cp) rings, or derivatives thereof, such as indenyl, tetrahydroindenyl, fluorenyl and mixtures. In addition to the two Cp ligands, other groups can be attached to the metal center, most commonly halides and alkyls. The Cp rings can be linked together (so-called "bridged metallocene" structure), as in most polypropylene catalysts, or they can be independent and freely rotating, as in most (but not all) metallocene-based polyethylene catalysts. The defining feature is the presence of at least one and preferably two Cp ligands or derivatives. Metallocene catalysts can be employed either as so-called "neutral metallocenes" in which case an alumoxane, such as methylalumoxane, is used as a co-catalyst, or they can be employed as so-called "cationic metallocenes" which are neutral metallocenes which have been activated, e.g., ionized, by an activator such that the active catalyst species incorporates a stable and loosely bound non-coordinating anion as a counter ion to a cationic metal metallocene center. Cationic metallocenes are disclosed, for example, in U.S. Pat. Nos. 5,064,802; 5,225,500; 5,243,002; 5,321,106; 5,427,991; and 5,643,847; and EP 426 637 and EP 426 638, the disclosures of which are incorporated herein by reference to the extent permitted.

"Constrained geometry" is a term that refers to a particular class of organometallic complexes in which the metal center is bound by only one modified Cp ring or derivative. The Cp ring is modified by bridging to a heteroatom such as nitrogen, phosphorus, oxygen, or sulfur, and this heteroatom also binds to the metal site. The bridged structure forms a fairly rigid system, thus the term "constrained geometry". By virtue of its open structure, the constrained geometry catalyst can produce resins having long chain branching that are not possible with normal metallocene catalysts. Constrained geometry catalysts are disclosed, for example, in U.S. Pat. Nos. 5,064, 802 and 5,321,106. Constrained geometry catalysts can also be employed in neutral or cationic form and use methylalumoxane or ionization activators respectively in the same fashion as metallocenes.

Late transitional metal (e.g., Fe, Co, Ni, or Pd) bidentate and tridentate catalyst systems have also been developed. Representative disclosures of such late transition metal catalysts are found in U.S. Pat. No. 5,880,241 and its divisional counterparts U.S. Pat. Nos. 5,880,323; 5,866,663; 5,886,224; and 5,891,963, and WO 1998/030612; WO 1998/027124; WO 1999/046302; WO 1999/046303; and WO 1999/046304.

Single site catalysts such as early and late transition metal pre-catalysts typically require activation to form a cationic metal center by an organometal Lewis acid (e.g., an alkylaluminoxane as described herein, such as methylalumoxane or MAO).

Single site and metallocene compounds suitable for use in the present invention can be selected from the group consisting of metallocenyl or substituted metallocenyl compounds of Groups 3-10 generally, such as Fe, Co, Ni, Zn, V, Mn, etc.; for example the Group 4 transition metals of the Periodic Table, such as Ti, Zr, Hf and Rf. Such compounds include bicyclopentadienyl zirconium dichloride (bimetallocenyl zirconium dichloride) and ethylidene biindenyl zirconium dichloride, but a significant number of compounds are known in the art, some of which are specifically identified in U.S. Pat. No. 6,559,090 and U.S. Pat. No. 6,943,224 identified above, the listings of which are incorporated herein by reference to the extent permitted.

Support or carrier particles useful in the invention are typically fine particle size inorganic or organic compounds in the form of porous, granular or particulate solids having a large surface area. Inorganic materials are preferred, for example, silica, alumina, silica-alumina, zirconia, magnesia (magnesium oxide), magnesium chloride, pumice, talc, kieselguhr, calcium carbonate, calcium sulfate and mixtures thereof. Alternatively or in combination with inorganic materials, particulate organic materials can be used, including for example, polystyrene, polyethylene, polypropylene, polycarbonate and the like.

Suitable inorganic compounds include inorganic oxides, hydroxides or salts; porous oxides are preferred, including for example $SiO_2$, $Al_2O_3$, $MgO$, $ZrO_2$, $TiO_2$, $B_2O_3$, $CaO$, $ZnO$, $BaO$, $ThO_2$, $V_2O_5$, $Cr_2O_3$ and mixtures thereof, including for example $SiO_2$—$MgO$, $SiO_2$—$Al_2O_3$, $SiO_2$—$TiO_2$, $SiO_2$—$V_2O_5$, $SiO_2$—$Cr_2O_3$ and $SiO_2$—$TiO_2$—$MgO$. Alternatively, non-oxide particulates can be used, for example, magnesium dichloride. Preferred carriers or supports comprise $SiO_2$ or $Al_2O_3$ or $SiO_2$ and $Al_2O_3$ as major ingredient(s). The inorganic oxides or mixtures thereof may further comprise carbonates, sulfates, nitrates and oxides, including, for example, $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_2$, $Li_2O$, and the like, typically in small or minor amounts.

A support or carrier typically exhibits the following characteristics: a mean particle diameter of about 10 µm (microns) to about 300 µm, preferably about 20 µm to about 200 µm, for example about 30 µm to about 100 µm; a specific surface area of about 10 $m^2/g$ to about 1,000 $m^2/g$, preferably about 50 $m^2/g$ to about 700 $m^2/g$, for example at least about 100 $m^2/g$; a pore size of at least about 80 angstroms, preferably about 100 angstroms; and a pore volume of about 0.3 $cm^3/g$ to about 2.5 $cm^3/g$. In an alternative embodiment and if desirable for the specific catalyst which is to be produced, before use in the processes described herein the support or carrier can be calcined at about 100° C. to about 1,000° C., preferably about 150° C. to about 700° C.

A preferred support or carrier comprises $SiO_2$. However, the particular support or carrier can be selected by one skilled in the art of polymerization processes, such selection being influenced by the type of process in which the catalyst comprising the aluminoxane is to be used. In particular, the particle size of the preferred $SiO_2$ will depend on whether the catalyst is to be used in a gas-phase polymerization process, a slurry polymerization process, or a solution polymerization process. For example, preferably:

(A) for use in an olefin polymerization process, the $SiO_2$ has a porosity of about 0.2 to about 2.5 cc/g, more preferably about 0.3 to about 2.0 cc/g, and most preferably about 0.5 to about 1.5 cc/g, each being a measure of the mean pore volume as determined by the BET technique using nitrogen as a probe molecule;

(B) for use in a gas-phase olefin polymerization process, the $SiO_2$ has a mean particle diameter from about 20 microns to about 200 microns, more preferably from about 30 microns to about 150 microns and most preferably from about 50 microns to about 100 microns, each as measured by sieve analysis;

(C) for use in a slurry olefin polymerization process, the $SiO_2$ has an mean particle diameter from about 1 micron to about 150 microns, more preferably from about 5 microns to about 100 microns and most preferably from about 20 microns to about 80 microns, each as measured by sieve analysis; and (D) for use in a solution olefin polymerization process, the $SiO_2$ has an mean particle diameter from about 1 micron to about 40 microns, more preferably from about 2 microns to about 30 microns and most preferably from about 3 microns to about 20 microns, each as measured by sieve analysis.

When a support or carrier, such as $SiO_2$, is mixed with aluminoxane or is present in a reaction mixture when aluminoxane is formed, it is generally accepted that a reaction occurs between the $SiO_2$ and the aluminoxane resulting in the aluminoxane being chemically as well as physically bound to the carrier or support. In various embodiments of the present invention the support or carrier, preferably $SiO_2$, can be present during the reaction of the organoaluminum compound and the emulsified water or the support or carrier can be added to the reaction mixture during the course of the reaction or thereafter. If the aluminoxane and carrier are contacted with one another after the aluminoxane is formed, the aluminoxane can be separated from its reaction mixture, including one or more steps to separate the aluminoxane from unreacted components such as the organoaluminum, and to separate the aluminoxane from the solvent(s) employed during the reaction. If the solvent(s) are allowed to remain with the aluminoxane, the carrier or support can be conveniently added directly to the aluminoxane-solvent composition.

The reaction of $SiO_2$ and aluminoxane is carried out in a solvent, preferably an inert solvent, under an inert atmosphere, preferably argon or nitrogen.

If the $SiO_2$ is not present during formation of the aluminoxane, the order of addition of the $SiO_2$ and aluminoxane and solvent is not critical, and aluminoxane can be added to a slurry of $SiO_2$ in the inert solvent or vice versa. It is also preferred that the $SiO_2$ and aluminoxane mixture be stirred throughout the reaction in order to expedite the reaction process by providing and maintaining an intimate contact between the reactants.

The contact or reaction between $SiO_2$ and aluminoxane may be performed at temperatures greater than about 40° C. to about 150° C., preferably about 40° C. to about 140° C., more preferably about 40° C. to about 110° C., alternatively about 40° C. to about 80° C., all preferably at about atmospheric pressure. The time of the reaction between $SiO_2$ and aluminoxane may be from about 15 minutes (min.) to about 24 hours, preferably from about 30 min. to about 12 hours, more preferably from about 1 hour to about 8 hours, and most preferably from about 2 hours to about 4 hours, in accordance with the conditions of temperature and pressure set forth above.

The silica is preferably dehydroxylated prior to reaction with aluminoxane. Dehydroxylation may be accomplished by any suitable means known in the art. A preferred means for the dehydroxylation reaction is heating of a silica powder in a fluidized bed reactor, under conditions well known to those skilled in the art. Most preferably, conditions are chosen such that the silica is substantially completely dehydroxylated prior to reaction with aluminoxane but, to be useful herein it is not required that the silica be completely dehydroxylated.

As noted above, surfactants are known to enhance the stability of an emulsion. A surfactant may be employed in accordance with the present invention to enhance the stability of the water-in-oil emulsion used to produce aluminoxane, particularly to impart improved stability of the emulsion over time. One or more suitable emulsifiers are used in the processes of the invention. Such emulsifiers are selected from surfactants capable of forming water-in-oil emulsions, typically those exhibiting hydrophilic-lypophilic balance (HLB) values of about 2 to about 10; preferably about 3 to about 9, such as those having HLB values of about 4 to about 8; such as about 5 to about 7; for example about 2 to about 5 or about 3, 4 or 5. Suitable surfactants have an HLB value selected from the group consisting of about 2, 2.5, 3, 3.5, 4, 4.5, 5, 5.5, 6, 6.5, 7, 7.5, 8, 8.5, 9, 9.5 and about 10. Examples of suitable emulsifiers include nonionic surfactants such as polyols and polyoxyethylenes.

Surfactants or emulsifiers useful in the processes of the present invention can react with organoaluminum compounds used in the process to form alkoxy aluminium compounds. Alternatively, a small amount of the aluminoxane can react, chelate or coordinate with the emulsifier and thus become strongly bound to it. The presence of such modified aluminoxane in the overall aluminoxane produced does not adversely affect the use of the finished catalyst products in the polymerization of olefins, particularly where the aluminoxane produced according to the processes of the present invention includes a step wherein the aluminoxane reaction product is extracted or washed with an inert solvent. Extraction can remove trimethylaluminum and/or chelated coordination compounds and is desirably carried out when the aluminoxane is supported.

The following tabulation provides examples of surfactants contemplated by the invention, although useful surfactants are not limited to those specifically identified, provided the surfactant or emulsifier is suitable for use with the reactants to produce the aluminoxane under the reaction conditions described. In other words, that the surfactant or mixture of surfactants forms a stable or substantially stable water-in-oil emulsion and does not adversely affect the catalytic utility of the resulting aluminoxane. Particularly useful compounds are generally characterized as esters of long chain carboxylic acids.

Surfactants are typically characterized according to the scale referred to as the hydrophilic-lipophilic balance or HLB. Traditional values according to the HLB scale range from 0 (strongly lipophilic) to about 20 (strongly hydrophilic). Surfactants or emulsifiers useful in the present invention are generally referred to as lipophilic or water-in-oil (W/O) emulsifiers and exhibit HLB values of less than about 10; for example, about 2 to about 8; or about 3 to about 7; or about 4 to about 6; or about 3 to about 6.

However, mixtures of W/O emulsifiers with oil-in-water (O/W) emulsifiers (HLB values greater than about 10, for example greater than about 11) can be prepared for which the overall HLB value is suitable for use in the present invention, in other words a value less than about 10, or in one of the other ranges recited above. Thus a person skilled in the art can select emulsifiers from a broad range of commercially available products in order to obtain at least one emulsifier useful with the oil selected for preparing the water-in-oil emulsion for introduction of water to the reaction with the selected organoaluminum compound.

Thus a broad range of surfactants are useful, including: glycerol monocaprylate, glycerol monolaurate, glycerol mono/dicocoate, glycerol dilaurate, glycerol monostearate, glycerol monostearate distilled, glycerol distearate, glycerol monooleate, glycerol dioleate, glycerol trioleate, glycerol monoisostearate, glycerol monoricinoleate, glycerol monohydroxystearate, POE glycerol monostearate, acetylated glycerol monostearate, succinylated glycerol monostearate, diacetylated glycerol monostearate tartrate, modified glycerol phthalate resin, triglycerol monostearate, triglycerol monooleate, triglycerol monoisostearate, decaglycerol tetraoleate, decaglycerol decastearate, pentaerythritol monolaurate, pentaerythritol monostearate, pentaerythritol distearate, pentaerythritol tetrastearate, pentaerythritol monooleate, pentaerythritol dioleate, pentaerythritol trioleate, pentaerythritol tetraricinoleate, sorbitan monolaurate, POE sorbitan monolaurate, sorbitan monopalmitate, POE sorbitan monopalmitate, sorbitan monostearate, POE sorbitan monostearate, sorbitan tristearate, POE sorbitan tristearate, sorbitan monooleate, POE sorbitan monooleate, sorbitan sesquioleate, sorbitan trioleate, POE sorbitan trioleate, POE sorbitol hexaoleate, POE sorbitol oleate laurate, POE sorbitol polyoleate, POE sorbitol, beeswax-ester, sucrose monolaurate, sucrose cocoate, sucrose monomyristate, sucrose monopalmitate, sucrose dipalmitate, sucrose monostearate, sucrose distearate, sucrose monooleate, sucrose dioleate, lauryl lactate, cetyl lactate, sodium lauryl lactate, sodium stearoyl lactate, sodium isostearoyl-2-lactylate, sodium stearoyl-2-lactylate, calcium stearoyl-2-lactylate, sodium capryl lactate, lauryl alcohol, and cetyl alcohol.

In one embodiment the emulsifier or surfactant comprises at least one sorbitan ester. The sorbitan esters include sorbitan fatty acid esters wherein the fatty acid component of the ester comprises a carboxylic acid of about 10 to about 100 carbon atoms, and in one embodiment about 12 to about 24 carbon atoms. Sorbitan is a mixture of anhydrosorbitols, principally 1,4-sorbitan and isosorbide (Formulas I and II):

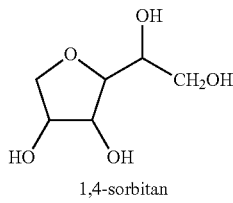

1,4-sorbitan (I)

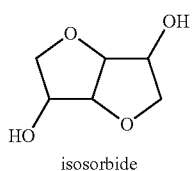

isosorbide (II)

Sorbitan, (also known as monoanhydrosorbitol, or sorbitol anhydride) is a generic name for anhydrides derivable from sorbitol by removal of one molecule of water. The sorbitan fatty acid esters of this invention are a mixture of partial esters of sorbitol and its anhydrides with fatty acids. These sorbitan esters can be represented by the structure below which may be any one of a monoester, diester, triester, tetraester, or mixtures thereof (Formula III):

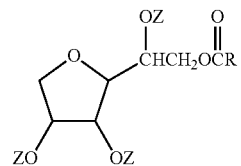

(III)

In formula (III), each Z independently denotes a hydrogen atom or C(O)R—, and each R mutually independently denotes a hydrocarbyl group of about 9 to about 99 carbon atoms, more preferably about 11 to about 23 carbon atoms. Examples of sorbitan esters include sorbitan stearates and sorbitan oleates, such as sorbitan stearate (i.e., monostearate), sorbitan distearate, sorbitan tristearate, sorbitan monooleate and sorbitan sesquioleate. Sorbitan esters are available commercially under the trademarks "Span" and "Arlacel" from ICI. The sorbitan esters also include polyoxyalkylene sorbitan esters wherein the alkylene group has about 2 to about 30 carbon atoms. These polyoxyalkylene sorbitan esters can be represented by Formula IV:

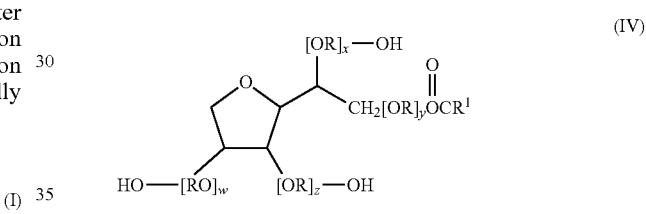

(IV)

wherein in Formula IV, each R independently is an alkylene group of about 2 to about 30 carbon atoms; R' is a hydrocarbyl group of about 9 to about 99 carbon atoms, more preferably about 11 to about 23 carbon atoms; and w, x, y and z represent the number of repeat oxyalkylene units. For example ethoxylation of sorbitan fatty acid esters leads to a series of more hydrophilic surfactants, which is the result of hydroxy groups of sorbitan reacting with ethylene oxide. One principal commercial class of these ethoxylated sorbitan esters are those containing about 2 to about 80 ethylene oxide units, and in one embodiment from about 2 to about 30 ethylene oxide units, and in one embodiment about 4, in one embodiment about 5, and in one embodiment about 20 ethylene oxide units. They are available from Calgene Chemical under the trademark "POLYSORBATE" and from ICI under the trademark "TWEEN". Typical examples are polyoxyethylene (hereinafter "POE") (20) sorbitan tristearate (Polysorbate 65; Tween 65), POE (4) sorbitan monostearate (Polysorbate 61; Tween 61), POE (20) sorbitan trioleate (Polysorbate 85; Tween 85), POE (5) sorbitan monooleate (Polysorbate 81; Tween 81), and POE (80) sorbitan monooleate (Polysorbate 80; Tween 80). As used herein the number within the parentheses refers to the number of ethylene oxide units present in the composition. As noted above, such high HLB surfactants or emulsifiers are primarily limited to use in mixtures with lower HLB surfactants in order to arrive at an overall HLB value suitable for use in the present invention.

The following is a list of emulsifiers that may be particularly useful:

| Product Name* | Synonym | HLB |
|---|---|---|
|  | 2,4,7,9-Tetramethyl-5-decyne-4,7-diol | 4.0 |
|  | PEG-block-PPG-block-PEG, Mn = 1100 | 4.0 |
|  | PEG-block-PPG-block-PEG, Mn = 2000 | 4.0 |
|  | PEG-block-PPG-block-PEG, Mn = 2800 | 4.0 |
|  | PEG-block-PPG-block-PEG, Mn = 4400 | 4.0 |
|  | Ethylenediamine tetrakis(PO-b-EO) tetrol, Mn = 3600 | 4.0 |
|  | Ethylenediamine tetrakis(EO-b-PO) tetrol, Mn = 7200 | 4.0 |
|  | Ethylenediamine tetrakis(EO-b-PO) tetrol, Mn = 8000 | 4.0 |
| Igepal CA-210 | Polyoxyethylene(2) isooctylphenyl ether | 4.3 |
| Span 80 | Sorbitan monooleate | 4.3 |
|  | PPG-block-PEG-block-PPG, Mn = 3300 | 4.5 |
| Igepal CO-210 | Polyoxyethylene(2) nonylphenyl ether | 4.6 |
| Span 60 | Sorbitan monostearate | 4.7 |
| Brij 92 | Polyoxyethylene(2) oleyl ether | 4.9 |
| Brij 72 | Polyoxyethylene(2) stearyl ether | 4.9 |
| Brij 52 | Polyoxyethylene(2) cetyl ether | 5.3 |
| Span 40 | Sorbitan monopalmitate | 6.7 |
| Merpol A surfactant | Nonionic, ethylene oxide condensate | 6.7 |
|  | 2,4,7,9-Tetramethyl-5-decyne-4,7-diol ethoxylate | 8.0 |
| Triton SP-135 |  | 8.0 |
| Span 20 | Sorbitan monolaurate | 8.6 |
|  | PEG-block-PPG-block-PEG, Mn = 5800 | 9.5 |
|  | PPG-block-PEG-block-PPG, Mn = 2700 | 9.5 |
| Brij 30 | Polyoxyethylene(4) lauryl ether | 9.7 |
| Igepal CA-520 | Polyoxyethylene(5) isooctylphenyl ether | 10.0 |
| Igepal CO-520 | Polyoxyethylene(5) nonylphenyl ether | 10.0 |
|  | Polyoxyethylene sorbitol hexaoleate | 10.2 |
| Merpol SE surfactant |  | 10.5 |
| Tween 85 | Polyoxyethylene(20) sorbitan trioleate | 11.0 |
|  | 8-Methyl-1-nonanol propoxylate-block-ethoxylate | 11.0 |
|  | Polyoxyethylene sorbitan tetraoleate | 11.4 |
| Triton X-114 | Polyoxyethylene (8) isooctylphenyl ether | 12.4 |
| Brij 76 | Polyoxyethylene(10) stearyl ether | 12.4 |
| Brij 97 | Polyoxyethylene(10) oleyl ether | 12.4 |
| Merpol OJ surfactant |  | 12.5 |
| Brij 56 | Polyoxyethylene(10) cetyl ether | 12.9 |
| Merpol SH surfactant |  | 12.9 |
|  | 2,4,7,9-Tetramethyl-5-decyne-4,7-diol ethoxylate (5 EO/OH) | 13.0 |
| Triton SP-190 |  | 13.0 |
| Igepal CO-630 | Polyoxyethylene(9) nonylphenyl ether | 13.0 |
| Triton N-101 | Polyoxyethylene branched nonylphenyl ether | 13.4 |
| Triton X-100 | Polyoxyethylene(10) isooctylphenyl ether | 13.5 |
| Igepal CO-720 | Polyoxyethylene(12) nonylphenyl ether | 14.2 |
|  | Polyoxyethylene(12) tridecyl ether | 14.5 |
|  | Polyoxyethylene(18) tridecyl ether | 14.5 |
| Igepal CA-720 | Polyoxyethylene(12) isooctyiphenyl ether | 14.6 |
| Tween 80 | Polyoxyethylene(20) sorbitan monooleate | 14.9 |
| Tween 60 | Polyoxyethylene(20) sorbitan monostearate | 15.0 |
|  | PEG-block-PPG-block-PEG, Mn = 2900 | 15.0 |
|  | PPG-block-PEG-block-PPG, Mn = 2000 | 15.0 |
| Brij 78 | Polyoxyethylene(20) stearyl ether | 15.3 |
| Brij 98 | Polyoxyethylene(20) oleyl ether | 15.3 |
| Merpol HCS surfactant |  | 15.5 |
| Tween 40 | Polyoxyethylene(20) sorbitan monopalmitate | 15.6 |

-continued

| Product Name* | Synonym | HLB |
|---|---|---|
| Brij 58 | Polyoxyethylene(20) cetyl ether | 15.7 |
|  | Polyoxyethylene(20) hexadecyl ether | 15.7 |
|  | Polyethylene-block-poly(ethylene glycol), Mn = 2250 | 16.0 |
| Tween 20 | Polyoxyethylene(20) sorbitan monolaurate | 16.7 |
| Brij 35 | Polyoxyethylene(23) lauryl ether | 16.9 |
|  | 2,4,7,9-Tetramethyl-5-decyne-4,7-diol ethoxylate (15 EO/OH) | 17.0 |
| Igepal CO-890 | Polyoxyethylene(40) nonylphenyl ether | 17.8 |
| Triton X-405 | Polyoxyethylene(40) isooctylphenyl ether | 17.9 |
| Brij 700 | Polyoxyethylene(100) stearyl ether | 18.8 |
| Igepal CO-990 | Polyoxyethylene(100) nonylphenyl ether | 19.0 |
| Igepal DM-970 | Polyoxyethylene(150) dinonylphenyl ether | 19.0 |
|  | PEG-block-PPG-block-PEG, Mn = 1900 | 20.5 |
|  | PEG-block-PPG-block-PEG, Mn = 8400 | 24.0 |
|  | Ethylenediamine tetrakis(PO-b-EO) tetrol, Mn = 15000 | 24.0 |
|  | PEG-block-PPG-block-PEG, average Mn = ca. 14,600 | 27.0 |

*Abbreviations in the above table:
Mn = number average molecular weight;
PEG = polyethylene glycol;
PPG = polypropylene glycol;
EO = ethylene oxide;
PO = propylene oxide;
HLB = hydrophilic-lipophilic balance.

Useful emulsifiers of the types listed in the above table can be generically represented by the following classes of chemical compounds, members of which are commercially available and are suitable provided that they are used in accordance with the teachings herein such that stable emulsified compositions are produced:

(a) sorbitol esters of the general formula

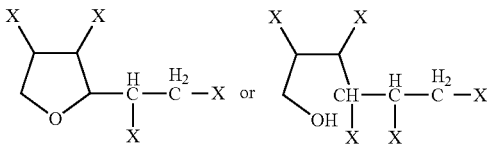

in which: the radicals X are identical to or different from one another and are each OH or $R^1COO^-$;

where $R^1$ is a linear or branched, saturated or unsaturated, aliphatic hydrocarbon radical optionally substituted by hydroxyls and having from 7 to 22 carbon atoms, provided that at least one of said radicals X is $R^1COO^-$, (b) fatty acid esters of the general formula:

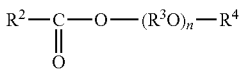

in which: $R^2$ is a linear or branched, saturated or unsaturated, aliphatic hydrocarbon radical optionally substituted by hydroxyl groups and having from 7 to 22 carbon atoms;

$R^3$ is a linear or branched $C_1$-$C_{10}$ alkylene;

n is an integer greater than or equal to 6; and $R^4$ is H, linear or branched $C_1$-$C_{10}$ alkyl or

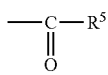

where $R^5$ is as defined above for $R^2$; and (c) polyalkoxylated alkylphenol of the general formula

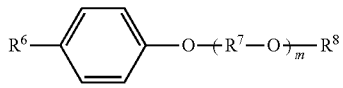

in which: $R^6$ is a linear or branched $C_1$-$C_{20}$ alkyl;

m is an integer greater than or equal to 8; and $R^7$ and $R^8$ are respectively as defined above for $R^3$ and $R^4$ of formula (II).

Particularly useful emulsifiers include compounds exhibiting a hydrophilic-lipophilic balance (HLB) typically in the range of about 0 to about 10; in another embodiment about 1 to about 9. HLB is defined in detail, for example, in the references "Emulsions: Theory and Practice, P. Becher, Reinhold Publishing Corp., ACS Monograph, ed. 1965", in the chapter "The chemistry of emulsifying agents" (pg. 232 et seq.); and also in Handbook of Applied Surface and Colloid Chemistry, K. Holmberg (Ed.), "Chapter 11, Surface Chemistry in the Petroleum Industry," J. R. Kanicky et al., 251-267, which also describes a method for calculating HLB values based on chemical structure; these references incorporated herein by reference to the extent permitted. A well established empirical procedure for determining HLB values for a given emulsifier may be determined experimentally by the method of W. C. Griffin, J. Soc. Cosmetic Chem., 1, 311 (1949), incorporated herein by reference to the extent permitted. Examples of suitable compounds are included in the above table and are also disclosed in McCutcheon's Emulsifiers and Detergents, 1998, North American Edition (pages 1-235) & International Edition (pages 1-199), incorporated herein by reference for their disclosure of compounds having suitable HLB values as described above. Various useful compounds include those identified in the above table, including for example, sorbitan monooleate, sorbitan monostearate and sorbitan monolaurate.

As discussed briefly above, it is also possible to obtain W/O emulsions suitable for the present invention using a combination of emulsifiers. For purposes of explanation and not limitation, for example instead of a single emulsifier having an HLB value of about 5, a water-in-oil emulsion can be prepared using a mixture of emulsifiers, such as a 50/50 mixture two emulsifiers, one having an HLB value of about 8 and the other an HLB value of about 2. Similarly combinations of three or more emulsifiers can also be used, provided that the HLB value of the mixture exhibits the desired overall value and the effect of the mixture is to provide a stable emulsion and not interfere with the catalytic value of the aluminoxane. For purposes of a mixed emulsifier composition, the HLB value of the emulsifier mixture is calculated as a linear sum weighted average based on the weight fraction that each of the emulsifiers represents compared to the total amount of emulsifier present:

$$HLB_m = \Sigma[(HLB_n)(wt_n/wt_{tot})]$$

where:

$\Sigma$=Sum of the values shown in brackets;

$HLB_m$=the HLB value of one or a mixture of emulsifiers;

n=number of emulsifiers present in the mixture, wherein any number of emulsifiers can be used; typically n=1 to about 5; more typically 1 to about 4; or 1 to about 3; or 1 to about 2. For example, it is suitable to use mixtures of 2, 3 or 4 emulsifiers to obtain a stable emulsion;

$HLB_n$=the HLB value of a single emulsifier if n=1 or the HLB value of each emulsifier in a mixture of emulsifiers;

$wt_n$=the weight, for example in grams, of each emulsifier in a mixture of emulsifiers; and $wt_{tot}$=the total weight of all emulsifiers present in a mixture of emulsifiers.

In an alternative embodiment a mixture of two emulsifiers is used wherein one emulsifier has an HLB value of equal to or less than about 6, for example about 1 to about 6.0, or about 2 to about 5.9, or about 3 to about 5.5, or about 4 to about 5.9, and the like; and the second emulsifier has an HLB value of greater than about 6, for example about 6 to about 10; or about 6.1 to about 9.5, or about 6.5 to about 8.5, or about 7 to about 8.5, and the like; provided that both emulsifiers do not have an HLB value of 6. Alternatively, one emulsifier comprising a bimodal distribution of chemical species exhibiting each of the HLB properties can be used.

The water used in the compositions of the present invention can be from any source. The water employed in preparing the W/O compositions of the present invention can be deionized, purified for example using reverse osmosis or distillation, and/or demineralized and have a low content of dissolved minerals, for example, salts of calcium, sodium and magnesium, and will similarly include little, if any, chlorine and/or fluorine as well as being substantially free of undissolved particulate matter. Preferably the water has been substantially demineralized by methods well known to those skilled in the art of water treatment in order to remove dissolved mineral salts and has also been treated to remove other additives or chemicals, including chlorine and fluorine. The substantial absence of such materials is desirable.

The water may be present in the water-oil emulsion at a concentration of about 5% to about 65% by weight of the water and oil; alternatively about 5% to about 60% by weight; about 10% to about 50% by weight; and about 15% to about 40% by weight of water. Expressed on a volume ratio basis, suitable levels of solvent (also referred to herein as diluent or oil), water and emulsifier for preparing the water-in-oil emulsion are typically about 100 (solvent):about 5 to about 100 (water):about 0.05 to about 20 (emulsifier); alternatively about 100 (solvent):about 10 to about 50 (water):about 0.5 to about 5 (emulsifier).

The water emulsion of the present invention (water, emulsifier or surfactant, and solvent or diluent) is prepared from the components described herein in processes that include mixing under high shear conditions to form an emulsion, the mixing preferably carried out using high mechanical shear or ultrasonic energy. Various mixing devices well known in the art can be employed to facilitate formation of an emulsified W/O compositions, for example, mixer-emulsifiers, which typically utilize a high speed rotor operating in close proximity to a stator (such as a type made by Charles Ross & Sons Co., NY), paddle mixers utilizing paddles having various design configurations including, for example, reverse pitch, anchor, leaf, gate, finger, double-motion, helix, etc., including batch and in-line equipment, and the like. Other methods of mixing useful in this embodiment as well as generally in the present invention are further described hereinbelow.

The processes of various embodiments for preparing an emulsion of the present invention can be carried out at a convenient temperature, including, for example, at ambient or room temperature, such as about 20° C. to about 22° C. or 25°

C. The time and temperature of mixing can be varied provided that the desired emulsified composition is achieved and, based on subsequent observation and/or testing, it is suitably stable until it is used, as well as during use.

Emulsions prepared under lower energy and shear conditions may contain dispersed particles having an average particle size, e.g., diameter or average dimension on the order of about 0.05 microns to about 100 microns.

In a preferred method, emulsions are prepared using ultrasonic mixing equipment, which equipment is particularly advantageous for preparing stable emulsions having a small particle size, for example less than about 10 microns, or about 0.05 to about 5 microns on average, sometimes referred to as a microemulsion, although such high shear devices can be used to prepare useful emulsions over the full range of useful particle sizes noted above. Preferred equipment of this type is available commercially as "Sonolator" ultrasonic homogenizing system, Sonic Corp., Conn. Such microemulsions can be prepared at ambient temperature, for example about 22° C., and at pressures of about 500 psi to about 1500 psi, although pressures as high as 5000 psi can also be used to produce stable microemulsions. The Sonolator system is particularly useful in that it can be operated in alternative, useful modes, including semi-continuous, continuous, single-feed or multiple-feed. In particular, such a system operated in multiple-feed mode can utilize feed tanks containing, for example, the oil or diluent, water, and emulsifier. Such a system allows feeding of one or more of the components simultaneously, sequentially or intermittently in order to achieve a particularly desirable result, including but not limited to a specific emulsion particle size, particle size distribution, mixing time, etc. A W/O composition prepared using ultrasonic emulsification can be accomplished using a lower concentration of emulsifier for the same concentration of other components, particularly the oil(s) or diluent(s) and water. The use of a device that introduces ultrasonic energy for mixing and emulsification is referred to herein as a "high shear" method, regardless of the physical processes that may occur on a microscopic or molecular scale.

High-shear devices that may be used include but are not limited to the Sonic Corporation Sonolator Homogenizing System, in which pressure can be varied over a wide range, for example about 500 to about 5,000 psi; IKA Work Dispax, and shear mixers including multistage, for example, three stage rotor/stator combinations. The tip speed of the rotor/stator generators may be varied by a variable frequency drive that controls the motor. Silverson mixer two-stage mixer, which also incorporates a rotor/stator design and the mixer employs high-volume pumping characteristics similar to a centrifugal pump. In-line shear mixers employing a rotor-stator emulsification approach (Silverson Corporation); Jet Mixers, venturi-style/cavitation shear mixers; Microfluidizer shear mixers, high-pressure homogenization shear mixers (Microfluidics Inc.); and any other available high-shear generating mixer capable of producing the desired microemulsion, including high shear mixers selected from the group consisting of Aquashear mixers (Flow Process Technologies Inc.), pipeline static mixers, hydraulic shear devices, rotational shear mixers, ultrasonic mixing, and combinations thereof.

The aluminoxane can be produced over a wide range of temperatures, from above the melting point of the solvent in which the organoaluminum compound is dissolved or of the diluent in which the water is dispersed as an emulsion, to up to the boiling point of the reaction mixture at the pressure used for carrying out the reaction. When very low temperatures are used frozen solids may be present in the reaction mixture; reaction can still occur, but it may occur at a slower rate in view of the multiple phases that are present. Generally, temperatures of about −80° C. to about 40° C. are suitable. A convenient temperature for carrying out the reaction is that of a dry ice/acetone bath, for example about −78° C. at ambient temperature and pressure. Low temperatures can be used with the appropriate choice of solvents or diluents, for example, about −20° C., about −40° C., about −60° C. or lower. Typically, the temperature during initial contact between the water containing emulsion and the organoaluminum solution is about −70° C. to about 40° C. Useful reaction temperature ranges include about −75° C. to about 40° C.; about −65° C. to about 30° C.; about −55° C. to about 20° C.; for example, about −45° C. to about 20° C.; about −15° C. to about 40° C.; about −10° C. to about 30° C.; about −5° C. to about 20° C. and about 0° C. to about 20° C. Reaction pressure is not critical and can be conveniently selected from normal atmospheric pressure to about 500 psi.

The supported catalysts prepared according to the process of the invention are suitable for use in the polymerization or copolymerization of olefins. Generally useful olefins include ethylene, $C_3$ to about $C_{20}$ alpha-olefins (or 1-olefins), cyclic olefins and dienes. Suitable monomers for use in the polymerization processes are, for example, ethylene, propylene, butene, hexene, methyl methacrylate, methyl acrylate, butyl acrylate, acrylonitrile, vinyl acetate, and styrene. Preferred monomers for homopolymerization processes are ethylene and propylene. The catalyst is especially useful for copolymerizing ethylene with other 1-olefins such as propylene, 1-butene, 1-hexene, 4-methylpentene-l, and octene. The catalyst can also be used for copolymerizing ethylene with styrene and/or styrene derivatives. Suitable polymerization processes include slurry polymerization, liquid bulk polymerization, gas phase polymerization, etc. Solvents useful in slurry polymerization processes may be saturated aliphatic hydrocarbons or aromatic hydrocarbons, and include hexane, heptane, cyclohexane and toluene. The polymerization can be carried out under ambient or high pressure and the polymerization pressure is typically from ambient pressure to about 10 MPa, for example, about 0.2 to about 5 MPa. Suitable polymerization temperatures are typically about −78° C. to about +275° C.; such as about +20° C. to about +150° C. The amount of the supported catalyst typically used during such polymerizations is about $10^{-7}$ to about $10^{-2}$ mol, based on the amount of the metal atom in the single site catalyst, for example, a metallocene. The polymerization process may be conducted continuously or in batch. Polymer molecular weight can be controlled by known methods during polymerization, such as by the selection of the temperature and pressure, and introduction of hydrogen into the polymerization system.

Supported catalysts prepared according to the processes of the invention can be used individually or in combinations of more than one for the polymerization of olefins, as well as in combination with metal alkyl compounds to further increase the activity or reduce or eliminate catalyst poisons. The metal alkyl compounds preferably used herein are triethyl aluminium and triisobutyl aluminium.

Supported, active single site catalysts comprising organometallic complex compounds and comprising the novel aluminoxane described herein can be prepared according to methods generally known in the art for preparing supported catalysts using aluminoxane prepared according to prior art methods. For example, U.S. Pat. No. 5,880,056 (T. Tsutsui et al.), incorporated herein to the extent permitted, discloses preparation of a supported catalyst by contacting an aluminoxane and/or a transition metal compound with a fine particle carrier in an inert solvent. Considering the options disclosed hereinabove, several alternatives are available for preparing active catalysts. For example, aluminoxane can be prepared according to the present invention in the absence of a carrier and then the aluminoxane can be contacted with a carrier, preferably in an inert diluent, before or after one or more single site or transition metal compounds is contacted with the carrier, preferably before. Alternatively, the aluminoxane can be prepared in the presence of a carrier and the supported aluminoxane contacted in an inert diluent with one or more single site or transition metal compounds.

The processes of the present invention can provide supported single site/aluminoxane solid catalysts such as metallocene/aluminoxane solid catalysts, at a high yield and with good reproducibility, directly from organoaluminium compounds as starting materials and require simple apparatus which are easy to operate. The supported catalysts obtained have high activity and are suitable for a variety of polymerization processes. The polymers obtained from the polymerization of olefins catalyzed by the catalysts of the invention have desirable morphology.

The following examples are provided as specific illustrations of embodiments of the claimed invention. It should be understood, however, that the invention is not limited to the specific details set forth in the examples. It should be understood, however, that the invention is not limited to the specific details set forth in the examples. All parts and percentages in the examples, as well as in the specification, are by weight unless otherwise specified. Furthermore, any range of numbers recited in the specification hereinabove or in the paragraphs referring to various aspects of the invention, as well as in the claims hereinafter, such as that representing a particular set of properties, units of measure, conditions, physical states or percentages, is intended to literally incorporate expressly herein by reference or otherwise, any number falling within such range, including any subset of numbers or ranges subsumed within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% . . . 50%, 51%, 52% . . . 95%, 96%, 97%, 98%, 99%, or 100%. Moreover, any numerical range represented by any two values of R, as calculated above is also specifically disclosed.

EXAMPLES

The following are the general procedures used in the examples described below. Unless otherwise specified, all operations were run under inert atmosphere such as in a glove box.

Bench scale polymerization (BSR) was carried out in a 2 L ZipperClave® reactor (Autoclave Engineers, Erie, Pa.). The reactor was remotely controlled using a desktop computer running Wonderware version 7.1 software program. Materials were handled and preloaded in a Vacuum Atmosphere glove box. The reactor body was prepared by preheating the unit to the desired internal temperature. Temperature control of the reactor was maintained by a Neslab RTE-111 (Thermo Fisher Scientific) heating/cooling bath. To make the unit's atmosphere inert and to aid in the drying of the internal parts, the equipment was placed under vacuum. The vacuum was generated by means of an Edwards E2M8 vacuum pump (Edwards High Vacuum UK). The initial vacuum reading was about 100 millitore of vacuum.

Test polymerization was typically conducted using the desired catalyst in order to polymerize ethylene. To start a polymerization test the following steps were used: heptane, hexene, and co-catalyst (i.e., used as a scavenger) are loaded into a pressure/vacuum rated glass "Pop" bottle inside of the glove box so that no air or moisture are introduced into the reactor. This mixture is removed from the dry box and then transferred into the test unit utilizing the reactor's internal vacuum to draw the solution into the reactor. The reactor's double helical stirrer is started and the computer program is initiated to begin controlling the water bath so the desired internal temperature is maintained. While the temperature re-stabilizes a 75 ml metal Hoke bomb is loaded inside the glove box with a slurry of the desired catalyst loading and 20 ml heptane. This container is removed from the glove box and connected to the injection port by using an external supply of argon to pre-purge all piping connections. The desired levels of ethylene and hydrogen gases are then introduced into the reaction vessel using the computer to add and monitor the unit pressure. The catalyst/heptane slurry is blown into the reactor using the high pressure argon gas supply. The software program is then set to control the final reaction pressure by remotely adding more ethylene gas to maintain a constant internal pressure. A typical test lasts for one hour from this point. When the polymerization test is finished the gas supply is shut off, the Neslab bath is shut off, and cooling water is introduced to the reactor jacket. Once the internal temperature has dropped below 50° C. the stirrer is stopped, all gases are vented from the unit, and the cooling water is stopped. The reactor body is then opened to remove the polyethylene product. The internal reactor wall and stirrer are then cleaned. The unit is resealed and pressurized with argon gas to ensure no leaks are present in the system. Once the unit has passed this pressure test the argon is vented, the reactor is placed back under vacuum, and reheated via the Neslab bath to prepare for the next test cycle.

In order to characterize polymers made according to the above synthesis procedure, the following tests were used to measure the following properties: Melt Index (MI) and high load melt index (HLMI) are measured according to ASTM method D1238-04. Melt flow ratio is defined as the value obtained based on HLMI/MI. Apparent bulk density (ABD) was measured according to ASMT method D1895.

The following examples were carried out:

Example 1

Invention; MAO/Silica Preparation

A water-in-oil emulsion was prepared as follows (not under an inert atmosphere).

A mixture of de-ionized water (2.00 g), white paraffin oil (VWR, VW3337-01, 4.10 g), and the emulsifier Span 80 (Aldrich, 0.10 g) were placed in a 50 mL caped plastic jar was vigorously shaken for 2 minutes on a Spex 8000 mixer. A stable white emulsion was formed that contained about 32.2 wt % water.

Supported methylaluminoxane (MAO) was prepared as follows.

To a 100 mL Schlenk flask was added silica (Sylopol 2485, Grace Davison), surface area about 300 m2/g, calcined at 600° C., 3.00 g) and toluene (Aldrich, anhydrous, 15 mL). Trimethylaluminum (TMA, Aldrich, 2.0M in toluene, 5.978 g, 14.76 mmol) was added slowly. The mixture was stirred for about 30 minutes at room temperature, and then cooled with ice-water bath. The above-described emulsion (0.686 g, 12.3 mmol water) was added dropwise to the flask while stirring with a magnetic stir bar. A uniform white suspension was formed with no visible chunks or agglomerates at bottom of the flask. The mixture was heated to reflux and heating continued for about 1 hr. The flask containing the reaction mixture was allowed to cool to room temperature and filtered through a frit. The resulting solids were washed with toluene (about 7 mL), followed by washing 3 times with heptanes (about 7 mL each), and dried under vacuum at room temperature to afford product as a white powder (3.76 g).

Example 2

Invention; Catalyst Preparation

Bis(n-butylcyclopentadienyl)zirconium dichloride (nBuCp2ZrCl2, WR Grace, Stenungsund, 14.62 mg, 0.036 mmol) dissolved in toluene (about 5 mL) was added to a slurry of above silica supported methylaluminoxane (2.20 g) in toluene (about 10 mL) while stirring at room temperature. The mixture was stirred for 1.5 hr at room temperature to give a yellow precipitate and colorless solution. The mixture was filtered. The resulting solid was washed with toluene (once, 7 mL), then heptanes (twice, 7 mL each), and dried under vacuum at room temperature to give product as a yellowish powder (2.0 g). The solid was found to contain 9.86 wt % of aluminum by Inductively Coupled Plasma (ICP) spectrometry analysis.

Example 3

Comparative; Supported MAO Preparation

Same as Example 1 except that de-ionized water (0.221 mL, 12.3 mmol) was added directly without emulsification via a micro-syringe. White chunks or agglomerates of undefined composition were formed at the bottom of the flask before the mixture was heated to reflux. This would be problematic at manufacturing scale for obtaining a uniform product. Product (3.47 g) was obtained as a white powder; aluminum content, 9.38 wt %.

Example 4

Comparative, Supported MAO Preparation

Same as Example 3 except that a lesser amount of water (0.177 mL, 9.84 mmol) was used. Product was found to contain 8.53 wt % aluminum).

Example 5

Comparative, Catalyst Preparation

Same as Example 2 except that MAO of Example 3 was used in place of the MAO of Example 1.

Example 6

Comparative, Catalyst Preparation

Same as Example 2 except that MAO of Example 4 was used in place of the MAO of Example 1.

Example 7

Inventive, Methylaluminoxane Initially Prepared in the Absence of a Support, then Supported Similar to the procedures in Examples 2 and 3 above. Aluminoxane was prepared first, silica was then added, and lastly metallocene was deposited:

To a 100 mL Schlenk flask with a magnetic stir bar was added TMA (2.0M in toluene, 9.96 g, 24.6 mmol) and toluene (20 mL). Emulsified water prepared as described above (1.143 g, 20.4 mmol water) was added drop-wise while the flask was cooled in an ice-water bath. The mixture was stirred for about 10 minutes in the ice-water bath then 2 hours at room temperature. Silica (5.0 g) was then added while stirring. The resulting slurry was stirred at room temperature for about 10 minutes, followed by heating to reflux and continued heating for about 4 hours. The flask was allowed to cool to room temperature and the liquid was removed by decanting. The solid was washed twice with toluene and decanted. The solid was then slurried in toluene (about 15 mL). Metallocene (nBuCp2ZrCl2, as above, 36.6 mg, 0.090 mmol) in toluene (about 10 mL) was added. The mixture was stirred at room temperature for about 3 hours. Liquid was decanted and the solid was washed three times with heptanes and decanted. The solid was then dried under vacuum to give a pale yellow powder product (4.5 g).

Example 8

(Comparative, same procedure as Example 7 except that un-emulsified water (0.367 g, 20.4 mmol) was used. White chunks or agglomerates of undefined composition were formed before silica was added and heated to reflux. This would be problematic at manufacturing scale for obtaining a uniform product.

Elemental analysis (Inductively Couple Plasma analysis, ICP) and polymerization data for the above-synthesized catalysts are summarized in the attached table. It is clear that using emulsified water was advantageous for producing uniform and active activators useful for making olefin polymerization catalysts.

| Catalyst | Activity (g/g-hr) | ABD | MI | HLMI | MFR | ICP (wt %) Al | Zr |
|---|---|---|---|---|---|---|---|
| Ex. 6/Ex. 4 (Comparative) Al/O = 1.5 | 209 | n/a | n/a | n/a | | 8.53 | |
| Ex. 5/Ex. 3 (Comparative) Al/O = 1.2 | 568 | n/a | 0.4 | 6.82 | 17.05 | 9.38 | |
| Ex. 2 (Inventive) Al/O = 1.2 | 2287 | 0.213 | 0.91 | 15.02 | 16.51 | 9.55 | 0.138 |
| Ex. 2 repeat | 2183 | 0.22 | 0.87 | 15.38 | 17.68 | | |
| Ex. 1 MAO only* | 68 | n/a | | n/a | | 9.86 | |
| Ex. 7 (Inventive) with emulsifier | 2099 | 0.262 | 0.88 | 13.88 | 15.77 | 9.06 | 0.144 |
| Ex. 7 repeat | 2008 | 0.272 | 0.89 | 13.67 | 15.36 | | |
| Ex. 8 (Comparative) no emulsifier | 1969 | 0.219 | 0.84 | 13.01 | 15.44 | 9.42 | 0.143 |

*MAO activator only, no single site transition metal complex

As shown in the above table MAO alone has effectively no polymerization activity; this provides a baseline reference. Catalyst from inventive example 2 exhibited a much higher activity, 2200 g/g-hr, compared to 209 g/g-hr and 568 g/g-hr of the comparative examples where a water-in-oil emulsion was not used. Inventive example 7 afforded comparable activity to that of comparative example 8, which confirms that the use of emulsifier in the preparation of MAO, which presumably remains in the catalyst composition, does not impair performance of the catalyst. In addition, the catalyst of the invention produced resins having desirably higher apparent bulk density (ABD) values, about 0.27.

The procedures described in the above examples of the invention are followed in order to prepare homopolymers, for example using propylene or styrene, as well as to prepare copolymers comprising, for example, ethylene and propylene or ethylene with other alpha-olefins and olefins and copolymers of propylene with other, higher olefins disclosed hereinabove.

The term "about" when used as a modifier for, or in conjunction with, a variable, characteristic or condition is intended to convey that the numbers, ranges, characteristics and conditions disclosed herein are flexible and that practice of the present invention by those skilled in the art using temperatures, rates, times, concentrations, carbon numbers, amounts, contents, properties such as size, density, surface area, etc., that are outside of the stated range or different from a single stated value, will achieve the desired result or results as described in the application, namely, the preparation of uniform and active aluminoxane activators useful for making olefin polymerization catalysts.

For purposes of the present invention the following terms shall have the indicated meaning:

"Comprise" or "comprising": Throughout the entire specification, including the claims, the word "comprise" and variations of the word, such as "comprising" and "comprises," as well as "have," "having," "includes," "include" and "including," and variations thereof, means that the named steps, elements or materials to which it refers are essential, but other steps, elements or materials may be added and still form a construct within the scope of the claim or disclosure. When recited in describing the invention and in a claim, it means that the invention and what is claimed is considered to what follows and potentially more. These terms, particularly when applied to claims, are inclusive or open-ended and do not exclude additional, unrecited elements or methods steps.

"Group" or "Groups": Any references to a Group or Groups shall be to the Group or Groups as reflected in the Periodic Table of Elements using the IUPAC system for numbering groups of elements as Groups 1-18.

"Periodic Table": All reference to the Periodic Table of the Elements herein refers to the Periodic Table of the Elements, published by the International Union of Pure and Applied Chemistry (IUPAC), published on-line at http://old.iupac.org/reports/periodic_table/; version date 22 Jun. 2007.

"Substantially": Unless otherwise defined with respect to a specific property, characteristic or variable, the term "substantially" as applied to any criteria, such as a property, characteristic or variable, means to meet the stated criteria in such measure such that one skilled in the art would understand that the benefit to be achieved, or the condition or property value desired is met.

All documents described herein are incorporated by reference herein, including any patent applications and/or testing procedures. The principles, preferred embodiments, and modes of operation of the present invention have been described in the foregoing specification.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A process for preparing aluminoxane comprising:
   (a) bringing into contact under reaction conditions in an inert atmosphere a reaction mixture comprising:
      (i) a water in oil emulsion comprising water and at least one emulsifier in a first hydrocarbon solvent; and
      (ii) an organoaluminum compound capable of forming aluminoxane in a second hydrocarbon solvent;
   wherein:
   (b) the molar ratio of the organoaluminum compound to water present in the emulsion is about 0.6 to about 2:1; and
   (c) the aluminoxane produced by the reaction is present in solution;
   provided that the first and second hydrocarbon solvents in step (a) maintain the aluminoxane in solution under the reaction conditions.

2. The process of claim 1 wherein the water in oil emulsion is prepared by combining a first inert solvent, water, and at least one emulsifier to form an emulsion and wherein the volume ratio of said first solvent, water, and emulsifier is about 100 (solvent):about 5 to about 100 (water):about 0.05 to about 20 (emulsifier).

3. The process according to claim 2, wherein said volume ratio of solvent, water, and emulsifier is about 100 (solvent):about 10 to about 75 (water):about 0.2 to about 10.0 (emulsifier).

4. The process according to claim 1, wherein the solution in step (a) (ii) comprises about 5 to about 40% by weight of the organoaluminum compound.

5. The process according to claim 1, wherein said molar ratio of the organoaluminum compound to water present in the emulsion is about 1 to 1.5:1.

6. The process according to claim 1, wherein the contact in step (a) is at a temperature of about −80° C. to about 40° C., provided that the reactive mixture comprises liquid.

7. The process according to claim 2, wherein the at least one emulsifier is a nonionic surfactant having a hydrophilic-lipophilic balance value of about 2 to about 6.

8. The process according to claim 1, wherein the organoaluminum compound is selected from the group consisting of alkyl aluminum, aryl aluminum and alkyl aluminum halide.

9. The process according to claim 8, wherein the organoaluminum compound is a trialkyl aluminum compound selected from the group consisting of a C1 to about C20 trialkylaluminum compound, trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, trihexylaluminum, trioctylaluminum and tridecylaluminum.

10. A process for preparing aluminoxane comprising:
   a) combining a first hydrocarbon solvent, water, and at least one emulsifier to form a water in oil emulsion:
      (i) wherein the volume ratio of said first hydrocarbon solvent, water, and emulsifier is about 100 (solvent):about 5 to about 100 (water):about 0.05 to about 20 (emulsifier);
   b) dissolving an organoaluminum compound capable of forming aluminoxane in a second hydrocarbon solvent to form a solution comprising about 5 to about 40% by weight of the organoaluminum compound;

c) contacting the emulsion and the solution with one another:
  (i) in a molar ratio of the organoaluminum compound to water in the emulsion of about 0.6 to about 2:1; and
  (ii) in an inert atmosphere;
to produce an aluminoxane solution, provided that the first and second hydrocarbon solvents present in steps (a) and (b) maintain the aluminoxane in solution under the reaction conditions in step (c).

11. The process according to claim 1 wherein a support carrier for the aluminoxane:
  (i) is present during said contact step (a); or
  (ii) is introduced following step (a).

12. The process according to claim 11 wherein the aluminoxane in the reactive mixture is heated to a temperature of greater than about 40° C. to about 150° C.

13. The process according to claim 12 wherein the reactive mixture is heated to a temperature at which reflux occurs.

14. The process according to claim 11 wherein the support carrier comprises at least one porous inorganic oxide selected from the group consisting of $SiO_2$, $Al_2O_3$, $MgO$, $ZrO_2$, $TiO_2$, $B_2O_3$, $CaO$, $ZnO$, $BaO$, $ThO_2$, $V_2O_5$, and $Cr_2O_3$.

15. The process according to claim 11 wherein the support carrier is $SiO_2$ and a Group 3 to Group 10 metal containing single site complex is mixed with the aluminoxane to produce a single site catalyst suitable for homopolymerizing an olefin, cyclic olefin, or alpha-olefin or copolymerizing an olefin, cyclic olefin or alpha-olefin with at least one $C_3$ to $C_{20}$ alpha-olefin monomer to form a polymer under olefin polymerization conditions.

16. The process according to claim 15 wherein the complex is a single site catalyst selected from the group consisting of constrained geometry complexes, metallocene complexes, bidentate complexes and tridentate complexes.

17. A process for preparing a supported catalyst comprising adding a solution of at least one metal containing single site complex compound in a solvent to the supported aluminoxane of claim 12 in a molar ratio of metal atom to aluminum atom of about 1:10 to 10,000 at about 0° C. to about 60° C. for about 1 to about 4 hours and removing the solvent to form said catalyst, wherein the metal is selected from a metal in Group 3 to Group 10 of the Periodic Table of the Elements.

18. The process according to claim 17, wherein said molar ratio of the metal atom in the complex to aluminum atom is about 1:50 to 1,000.

* * * * *